United States Patent [19]
Schwan

[11] 4,002,612
[45] Jan. 11, 1977

[54] 1-(3,4-DICHLOROBENZYL)HEXAHYDRO-1,3-DIAZEPIN-2(1H)-ONE

[75] Inventor: Thomas J. Schwan, Norwich, N.Y.

[73] Assignee: Morton-Norwich Products, Inc., Norwich, N.Y.

[22] Filed: Apr. 5, 1976

[21] Appl. No.: 673,374

[52] U.S. Cl. .......................... 260/239.3 R; 424/244
[51] Int. Cl.² ...................................... C07D 243/04
[58] Field of Search ............................. 260/239.3 R

[56] References Cited
FOREIGN PATENTS OR APPLICATIONS 1,130,904  10/1968  United Kingdom ........ 260/239.3 R

*Primary Examiner*—Henry R. Jiles
*Assistant Examiner*—Robert T. Bond
*Attorney, Agent, or Firm*—Anthony J. Franze

[57] ABSTRACT

The compound 1-(3,4-dichlorobenzyl)hexahydro-1,3-diazepin-2(1H)-one possesses activity as an anthelmintic agent.

1 Claim, No Drawings

1-(3,4-DICHLOROBENZYL)HEXAHYDRO-1,3-DIAZEPIN-2(1H)-ONE

The invention is concerned with the compound 1-(3,4-dichlorobenzyl)hexahydro-1,3-diazepin-2(1H)-one of the formula:

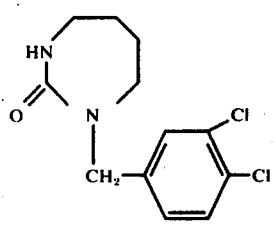

This compound possesses anthelmintic properties. When administered perorally to mice harboring *Ascaris suum* in a dose of 100 mg/kg b.i.d. for three days, an 83% reduction in worm population is secured.

In order that this invention may be available to and understood by those skilled in the art, the following method for its preparation is set forth:

1-(3,4-Dichlorobenzyl)hexahydro-1,3-diazepin-2(1H)-one

A mixture of 22.8 g (0.20 mole) of hexahydro-1,3-diazepin-2-one, 19.5 g (0.10 mole) of 3,4-dichlorobenzyl chloride, and 4.0 g g NaH (60% in mineral oil) (2.40 g, 0.10 mole) in 300 ml toluene was stirred at 95°–100° for 15 hr. The cooled mixture was diluted with 175 ml water and stirred for 15 min. The toluene layer was separated and the aqueous phase was extracted with 150 ml benzene. The combined organic extracts were washed with 150 ml water, dried over $MgSO_4$, and concentrated to dryness in vacuo to give 23 g of an oil. Crystallization from 350 ml heptane gave 8.0 g (29%) of the product, m.p. 100°–103°. Further recrystallization from heptane gave an analytical sample, m.p. 101°–103°.

Anal. Calcd. for $C_{12}H_{14}Cl_2N_2$: C, 52.76; H, 5.17; N, 10.26. Found: C, 52.76; H, 5.33; N, 10.18

What is claimed is:
1. 1-(3,4-Dichlorobenzyl)hexahydro-1,3-diazepin-2(1H)-one.

* * * * *